US000001228H

United States Statutory Invention Registration [19]

[11] Reg. Number: H1228

Doering

[43] Published: Sep. 7, 1993

[54] MEDICATED LOLLIPOP

[76] Inventor: Jodi Doering, R.R. #1, Site 9, Box 116, Grande Prarie, Canada, T8V-2Z8

[21] Appl. No.: 610,292

[22] Filed: Oct. 4, 1990

Related U.S. Application Data

[63] Continuation of Ser. No. 409,336, Sep. 19, 1989, abandoned.

[51] Int. Cl.[5] ..... A61K 9/68; A61K 9/16; A61F 13/00

[52] U.S. Cl. ..... 424/440; 424/435

[56] References Cited

U.S. PATENT DOCUMENTS

| | | | |
|---|---|---|---|
| 352,466 | 11/1886 | Huttemeyer | 424/35 |
| 1,046,056 | 12/1912 | Drake | 424/35 |
| 2,253,800 | 8/1941 | Myers et al. | 424/35 |
| 2,311,923 | 2/1943 | Lautmann | 424/35 |
| 2,580,683 | 1/1952 | Kreuger | 424/37 |
| 3,515,781 | 6/1970 | Steinberg | 424/37 |
| 3,536,074 | 10/1970 | Aufhauser | 424/37 |
| 3,644,613 | 2/1972 | Moeller et al. | 426/3 |
| 3,943,928 | 3/1976 | Lariccia et al. | 128/260 |
| 4,196,189 | 4/1980 | Raaf et al. | 424/37 |
| 4,260,596 | 4/1981 | Mackles | 424/440 |
| 4,292,304 | 9/1981 | Barels et al. | 424/37 |
| 4,372,942 | 2/1983 | Cimiluca | 424/16 |
| 4,551,329 | 11/1985 | Harris et al. | 424/22 |
| 4,671,953 | 6/1987 | Stanley et al. | 424/440 |
| 4,762,719 | 8/1988 | Forester | 424/440 |
| 4,847,090 | 7/1989 | Della Posta et al. | 424/440 |
| 4,863,737 | 9/1989 | Stanley et al. | 424/440 |

FOREIGN PATENT DOCUMENTS

| | | | |
|---|---|---|---|
| 799450 | 11/1968 | Canada | 424/37 |
| 829269 | 12/1969 | Canada | 424/37 |
| 1060258 | 3/1967 | United Kingdom | 424/440 |

*Primary Examiner*—Robert L. Stoll
*Assistant Examiner*—C. Harris

[57] ABSTRACT

A solid form of medication is in the form of a lollipop. The lollipop includes two spherical portions, one located inside the other. The inner portion can include medicine or candy.

3 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MEDICATED LOLLIPOP

This is a continuation of copending application Ser. No. 07/409,336, filed on Sep. 19, 1989, abandoned.

TECHNICAL FIELD OF THE INVENTION

The present invention relates to the general art of medicine, and to the particular field of medicated food-like items.

BACKGROUND OF THE INVENTION

At one time or another, nearly everyone has a cough or a sore throat. Many people take cough medicine or other throat-soothing medicine for such ailments.

These medications are packaged in both solid and liquid forms, and can be purchased through prescription or over-the-counter.

Taking cough medicine or throat medicine is extremely odious to many patients, such as young children or bedridden adults. While a solid form of medication has many advantages, it has a disadvantage in that a danger of choking on a swallowed solid form of medicine exists in both of these classes of patients.

Accordingly, there is a need for a solid form of cough or throat medicine which is in a form that makes it pleasant to take, yet does not have the same dangers of being swallowed as do the present form of lozenges or cough drops.

OBJECTS OF THE INVENTION

It is a main object of the present invention to provide a solid form of cough or throat medicine which is in a form that makes it pleasant to take.

It is another object of the present invention to provide a solid form of cough or throat medicine which is in a form that makes it pleasant to take yet does not have the same dangers of being swallowed as do the present form of lozenges or cough drops.

SUMMARY OF THE INVENTION

These, and other, objects are achieved by providing a cough medicine in the form of a lollipop, and by adding an inner portion of either a second medicine, such as a throat-soothing medicine or the like, or candy. The candy is used as an inducement to a young child to finish the medicine portion of the item.

DETAILED DESCRIPTION OF THE PREFERRED EMBODIMENT OF THE INVENTION

Figure 1:
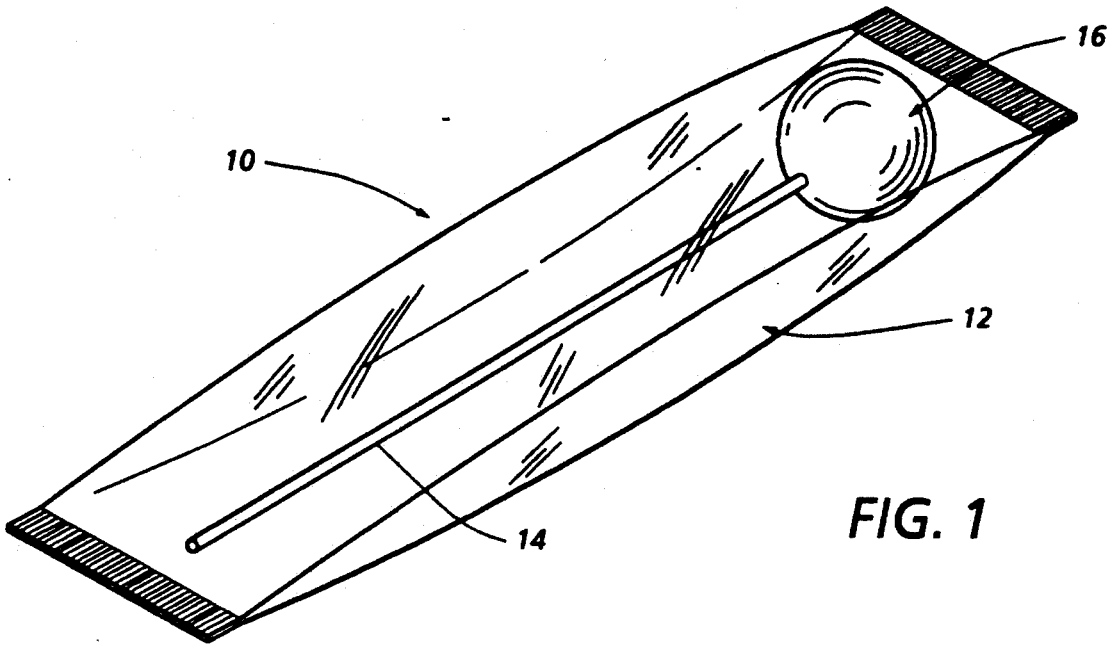
FIG. 1 is a perspective view of a medicated lollipop embodying the present invention, with a package for such item.
Figure 2:
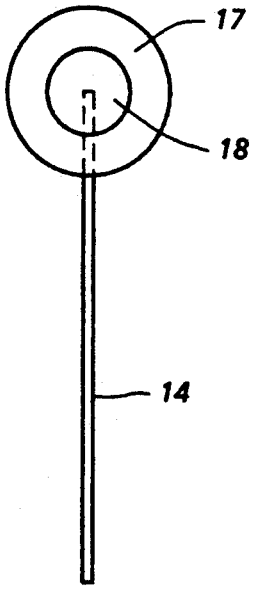
FIG. 2 is a side elevational view of the medicated lollipop of the present invention.

Shown in the figures is a lollipop 10 packaged in a translucent package 12. The lollipop includes a stick portion 14 on which is mounted a medicated portion 16. The medicated portion is spherical in form, and includes an outer spherical portion 17 which is formed of cough medicine and is adapted to taken in the manner of a lollipop. The exact type of medicine can vary from prescription medicine to over-the-counter medicine, and can be either cough medicine or throat-soothing medicine.

As shown, the lollipop 10 includes a second spherical portion 18 located within the first outer spherical portion. This second portion 18 can include a second medicine, such as throat medicine, headache medicine, fever medicine, or the like, or can include a sleeping medicine or an antihistamine. In this manner, the lollipop can provide a plurality of results.

Alternatively, the second portion 18 can include a candy food item. In this manner, a young child can be encouraged to finish the medicine contained in the first, outer, spherical portion.

It is understood that while certain forms of the present invention have been illustrated and described herein, it is not to be limited to the specific forms or arrangements of parts described and shown.

I claim:

1. A medicated item comprising:
   A) a first, outer spherical portion of cough medicine;
   B) a second, inner spherical portion of throat-soothing medicine type material; and
   C) a stick portion connected to both said first and said second spherical portions.

2. The medicated item defined in Claim 1 further including a translucent package.

3. A medicated item comprising:
   A) a first, outer spherical portion of cough medicine;
   B) a second, inner spherical portion of candy; and
   C) a stick portion connected to both said first and said second spherical portions.

* * * * *